United States Patent [19]
Cermak

[11] Patent Number: 5,941,889
[45] Date of Patent: Aug. 24, 1999

[54] MULTIPLE ANGLE DISPOSABLE NEEDLE GUIDE SYSTEM

[75] Inventor: Craig Cermak, Riverside, Iowa

[73] Assignee: CIVCO Medical Instruments Inc., Kalona, Iowa

[21] Appl. No.: 08/949,361

[22] Filed: Oct. 14, 1997

[51] Int. Cl.⁶ .................................................. A61B 19/00
[52] U.S. Cl. ........................................................ 606/130
[58] Field of Search ............................. 606/1, 108, 130; 604/116, 93; 600/641

[56] References Cited

U.S. PATENT DOCUMENTS

| | | | |
|---|---|---|---|
| 4,469,106 | 9/1984 | Harui | 128/660 |
| 4,733,661 | 3/1988 | Palestrant | 128/303 B |
| 4,899,756 | 2/1990 | Sonek | 600/461 |
| 4,911,173 | 3/1990 | Terwilliger | 128/662.06 |
| 5,076,279 | 12/1991 | Arenson et al. | 128/662.05 |
| 5,235,987 | 8/1993 | Wolfe | 128/662.05 |
| 5,623,931 | 4/1997 | Wung et al. | 128/662.05 |
| 5,758,650 | 6/1998 | Miller et al. | 600/461 |

*Primary Examiner*—Michael Buiz
*Assistant Examiner*—Vy Q. Bui
*Attorney, Agent, or Firm*—Merchant & Gould P.C.

[57] ABSTRACT

A needle guide for use in imaging analysis, such as ultrasound analysis, is provided having a bracket, a mounting base secured to the imaging instrument, and a pivoting portion configured to pivot along at least one axis. A disposable needle guide is configured to be removably secured to the pivoting portion of the mounting base. The needle guide has a needle retainer member that is configured to regain a needle by application of a clamping force between the needle retainer member and a first surface of the needle guide.

26 Claims, 3 Drawing Sheets

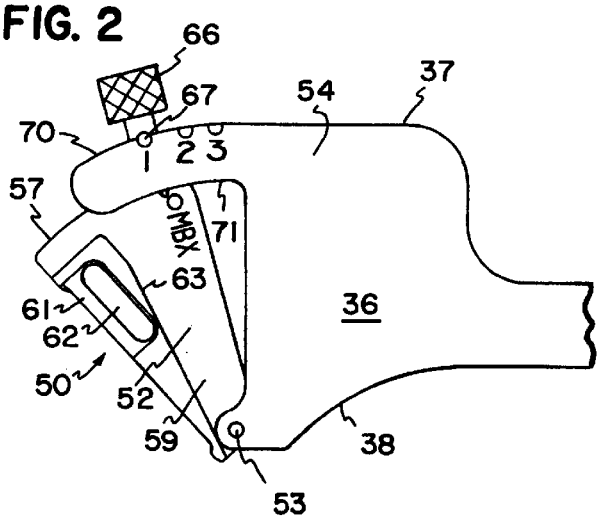
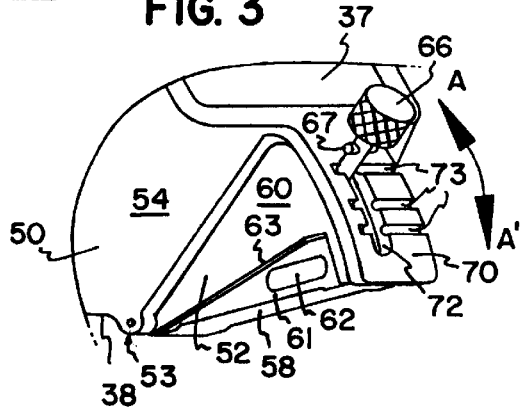
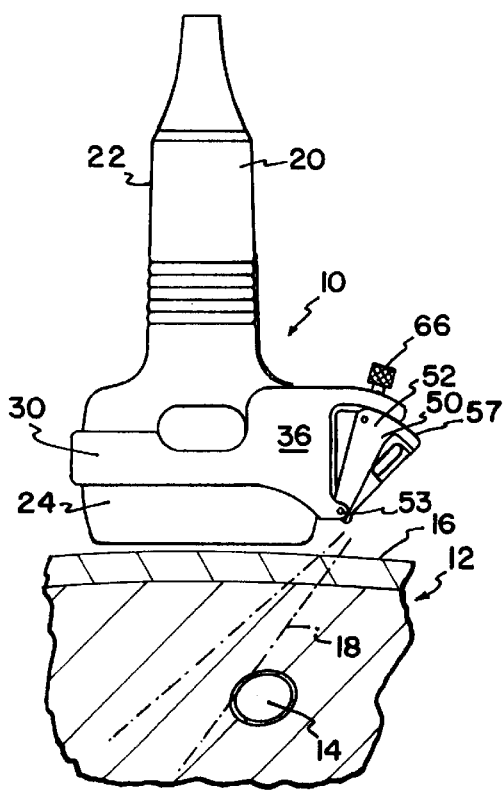
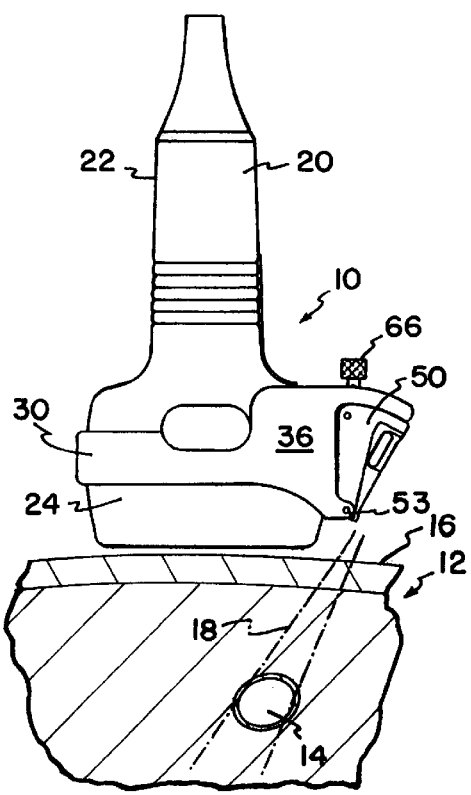

MULTIPLE ANGLE DISPOSABLE NEEDLE GUIDE SYSTEM

FIELD OF THE INVENTION

The present invention relates to a needle guide for a medical imaging instrument. More particularly, the invention is directed to a method and apparatus for a multiple angle disposable needle guide system for use in guiding needles into selected locations of a patient relative to a medical instrument imaging sensor.

BACKGROUND

Imaging instruments, such as ultrasound probes, computed tomography scanners (CT Scanners), and magnetic resonance imagers (MRI) have revolutionized the manner in which many important medical procedures are performed. Each of these medical instruments utilizes non-invasive imaging techniques to explore and assess the condition of sub-dermal tissue. As a result of this non-invasive imaging ability, diagnostic and therapeutic protocol's have been developed that allow for the provision of many highly successful and safe procedures with a minimum of disturbance to patients.

Ultrasound, for example, has received widespread acceptance as a useful diagnostic tool. Ultrasound is particularly well suited for obstetrics, where real-time scanners create a continuous image of a moving fetus that can be displayed on a monitoring screen. The image is created by emission of very high frequency sound waves from a transducer placed in contact with the mother's skin. Repeated arrays of ultrasonic beams scan the fetus and are reflected back to the transducer, where the beams are received and the data transmitted to a processing device. The processing device can analyze the information and compose a picture for display on the monitoring screen. Relative measurements may be made, and the gestational age, size and growth of the fetus can be determined. In some circumstances, a needle is guided into the amniotic fluid in order to retrieve a fluid sample for analysis. These samples can be useful for diagnosing irregular conditions and indicate that prenatal care is necessary for the fetus.

Ultrasound probes, and other imaging instruments, are also used for a variety of other purposes, such as identifying the existence, location, and size of tumors, as well as the existence of other medical conditions, including the atrophy or hypertrophy of bodily organs. While many imaging techniques are primarily performed on humans, similar techniques are often used by veterinarians to diagnose and treat a wide variety of animals, such as sheep, cows, horses, and pigs.

For many imaging applications, it is desirable that a needle, biopsy instrument, catheter, or other thin instrument be inserted into the body of a patient in order to remove a biopsy sample or to perform other medical procedures. It is normally desirable that the thin instrument or needle be guided to a specific position within the body of the patient. Various guide devices have been designed for assisting in guiding the instrument. Many of these guides are fixed-angle devices with limited functionality because they have limited control over needle placement compared to a needle guide that allows selection of multiple angles. In addition, many of these devices do not permit the placement of more than one needle into a patient or they do not make such multiple placements easy.

Another specific problem with many current needle guide systems is that they are not well suited to be used with a sterile cover, such as a latex film, placed over the imaging instrument. Such covers are increasingly desirable in order to maintain the ultrasound sensor in a sterile environment. The covers reduce the likelihood of contamination between patients and reduce the cost of medical procedures by minimizing sterilization costs. One challenge of working with latex and similar polymer based covers is that they have a high coefficient of friction and are subject to binding when in contact with moving pieces of an imaging sensor or needle guide. Such binding can lead to tears or punctures of the cover. For example, some prior art imaging sensors have removable pieces that are frictionally fit over a latex cover. Such designs are problematic because they can be difficult to fit and remove, as well as cause problems with binding and an ensuing risk of tearing.

Consequently, a need exists for an improved needle guide system. Such improved needle guide system should permit a needle to be directed into a patient at a variety of angles and allow for the easy removal of the needle from the system without damage to a protective cover.

SUMMARY OF THE INVENTION

The present invention is directed to a disposable needle guide system for use in guiding a needle into a patient who is undergoing imaging analysis. This disposable needle guide system includes a bracket, a mounting base, a pivoting portion of the mounting base, and a needle guide. The bracket is used to secure the needle guide system to an imaging instrument, such as an ultrasonic probe. The mounting base is secured to the imaging instrument by this bracket. While the bracket may be separable from the probe, it may also be integrally formed thereto and in essence be one piece with probe. The pivoting portion of the mounting base is configured to pivot along at least one axis, and the disposable needle guide is removably secured to the pivoting portion of the mounting base. The needle guide has a needle retainer member configured to retain a needle by application of a clamping force.

The needle guide system of the present invention is designed such that it may be used with a protective cover placed over the bracket and mounting base. The needle guide is configured to be removably secured to the mounting base over the protective cover, without the development of significant kinetic friction between the protective cover and the needle guide during mounting and removal of the needle guide. As such, the disposable needle guide may be placed on the pivoting portion of the mounting base, and removed therefrom, with minimal mechanical stress to the protective cover, thereby preventing holes in the protective cover from developing and maintaining a sterile environment around the imaging instrument.

In specific implementations of the present invention, the needle guide system further includes a movable locking member having an unlocked configuration in which the locking member does not apply pressure to the mounting base, while also having a locked configuration in which the locking member does apply pressure to the mounting base. The locking member may be alternated between a locked and unlocked configuration without applying significant kinetic friction to the protective cover.

In certain implementations, the pivoting portion of the mounting base pivots around an axis occupied by a pin. In other implementations, the pivoting portion is integrally connected to a non-pivoting portion of the base by a flexible connecting portion, and the pivoting portion pivots around an axis formed by flexing of the connecting portion. In this implementation, the pivoting portion does not pivot around a pin.

In certain embodiments of the present invention, the pivoting portion of the mounting base may be locked in one of a plurality of preset positions. Also, in specific implementations, the needle retainer member is slidably secured to the needle guide and is interchangeable with a second needle retainer member. Alternatively, the needle retainer member is integrally formed with the needle guide.

The needle retainer member pivots along an axis parallel to the length of the needle retainer member, permitting needles of multiple sizes to be held between the needle retainer member and a first surface of the needle guide. The needle is removed from the needle guide by release of the clamping force holding the needle in place.

A plurality of interchangeable needle retainer members are used in specific implementations of the present needle guide system so as to permit needles of various sizes to be used. The bracket of the present invention includes two paired arms for securing the needle guide system to an imaging instrument in specific implementations. As noted above, the bracket may be integrally formed with the imaging instrument to be one piece. The paired arms are configured to apply a compressive force to the imaging instrument, and the imaging instrument is an ultrasonic probe in specific implementations.

The above summary of the present invention is not intended to describe each discussed embodiment of the present invention. This is the purpose of the figures and the detailed description which follow.

BRIEF DESCRIPTION OF THE DRAWINGS

Other aspects and advantages of the invention will become apparent upon reading the following detailed description and references to the drawings, in which:

FIG. 2 is a fragmentary elevational view of a portion of a bracket and a needle guide mounting base, constructed in accordance with the present invention, showing a first side of the mounting base.

FIG. 3 is an fragmentary perspective view of a needle guide mounting base constructed in accordance with the present invention, showing a second side of the mounting base.

FIG. 4A is a side elevational view of a disposable needle guide system constructed in accordance with the present invention, showing the mounting base adjusted to a first position.

FIG. 4B is a side elevational view of a disposable needle guide system constructed in accordance with the present invention, showing the mounting base adjusted to a second position.

While the invention is susceptible to various modifications and alternative forms, specifics thereof have been shown by way of example and drawings, and will be described in detail. It should be understood, however, that the intention is not to limit the invention to particular embodiments described. On the contrary, the intention is to cover modifications, equivalents, and alternatives falling within the spirit and scope of the invention as defined by the appended claims.

DETAILED DESCRIPTION

Figure 1:
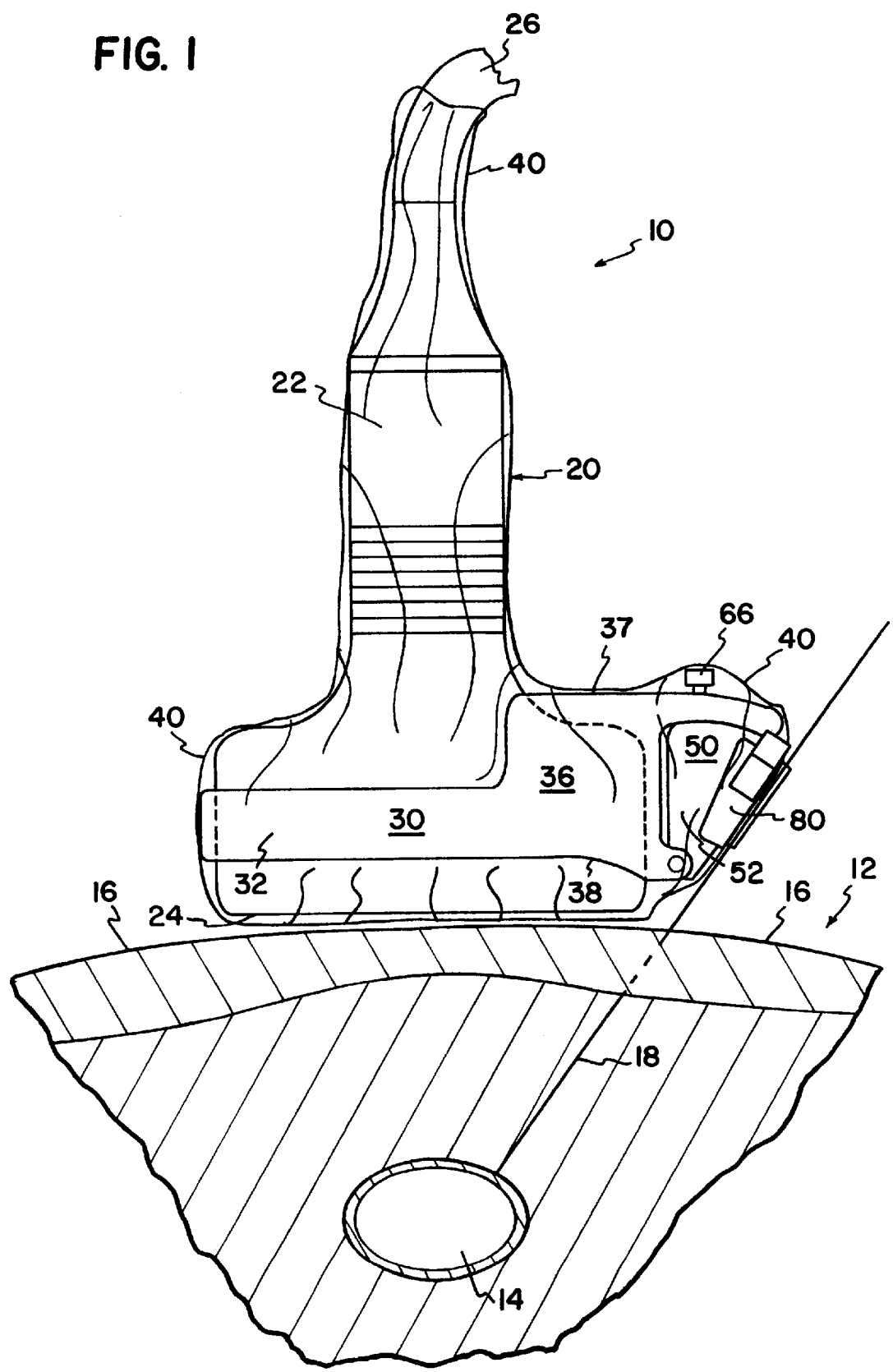
FIG. 1 is a side elevational view of a disposable needle guide system constructed in accordance with the present invention, showing the needle guide system installed on an ultrasonic probe having a protective cover.

Referring now to the figures wherein like numerals identify like elements throughout the drawings, FIG. 1 shows a side elevational view of a disposable needle guide system constructed in accordance with the present invention. Needle guide system 10 includes an ultrasound probe 20 onto which is secured a bracket 30. A protective cover 40 encases the ultrasonic probe 20 and the bracket 30, as well as the needle guide mounting base 50. A needle guide 80 is fitted over the protective cover 40 and onto the mounting base 50. Protective cover 40 provides a sterile seal over the ultrasound probe 20, bracket 30, and needle guide mounting base 50 such that these elements of the needle guide system 10 remain free of contamination during most medical procedures. As such, the enclosed elements of the needle guide system 10 do not come in contact with bodily fluids and reduce the risk of transfer of disease-causing vectors between the needle guide system and the patient.

The protective cover 40, which is normally disposable, thereby prevents contamination between patients as well as providing a low-cost method of reducing sterilization requirements of the ultrasound probe and needle guide system. The needle guide 80 is outside of the protective cover, and therefore is normally disposed of after the medical procedure or is sterilized using conventional methods between procedures.

Ultrasound probe 20 includes a handle 22 connected to a sensor 24. Handle 22 is typically configured to be grasped by the hand of a medical practitioner who is conducting an imaging analysis with the ultrasound probe 20. However, the handle 22 may alternatively be held, or additionally be held, by a mechanical brace or adjusting device for holding the ultrasound probe in a specific adjustable position. The sensor 24 includes an ultrasound transducer and receiver in specific implementations of the present invention, and sends out and receives sound waves that are transmitted to diagnostic and display equipment (not shown). Protective cover 40 is normally constructed of a thin polymer film, most often of natural or synthetic latex. While protective cover 40 will normally encompass the entire ultrasound probe, bracket 30 and needle guide mounting base 50, it is preferred that it include an opening at a cable terminus 26. Cable terminus 26 leads to the diagnostic and display equipment (not shown).

As is indicated in FIG. 1, the ultrasound probe 20 may be placed in a position proximate a patient 12. In FIG. 1, patient 12 is depicted in fractional view showing a target zone 14 and an outer surface or skin 16. Target zone 14 may be any of a number of locations within the body of a human or animal which is desirably accessed by a needle or other thin medical instrument, such as a catheter or biopsy probe. Target zone 14 may be, for example, a tumor of which a biopsy sample is desired, or a volume of amniotic fluid from which a sample is desired.

Bracket 30 is configured to securely retain the mounting base 50 and needle guide 80 to the ultrasound probe 20. While bracket 30 may have any of numerous configurations suitable for securing mounting base 50 and needle guide 80 to the ultrasound probe 20, in at least one implementation bracket 30 has first and second arms 32 on opposite sides of the ultrasound probe 20 (first arm 32 shown in FIG. 1). First and second arms 32 fit around opposing sides of the sensor 24 of the ultrasound probe 20 and provide a compressive force securing mounting base 50 and needle guide 80 by way of the bracket 30 and to the ultrasound probe 20.

Bracket 30 further comprises a body 36 proximate a needle guide mounting base 50. Body 36 is a portion of the bracket 30, and in certain implementations of the present invention is the portion of the bracket where the first and second arms 32 come together. In addition, in certain implementations, body 36 provides a location for a needle guide mounting base 50. Body 36 has a top portion 37 and a bottom portion 38. Bottom portion 38 is typically positioned proximate the body of the patient 12 when undergoing imaging analysis; while top portion 37 is typically positioned away from the patient 12, and proximate the hand of an operator of the ultrasound probe 20. As noted above, the bracket 30 may take numerous forms, including being integrally formed with the imaging instrument, or may be threaded to the imaging instrument, clipped on, etc.

The needle guide mounting base 50, mentioned above, is the portion of the needle guide system 10 that adjusts in angle in order to direct needles (or other medical instruments) at various orientations into the body of a patient 12. The needle guide 80 is secured or mounted to the mounting base 50. In certain implementations of the present invention, the needle guide 80 and mounting base 50 are integrally formed to one another. However, in other implementations, the needle guide 80 and mounting base 50 are separated from one another by the protective cover 40. In these implementations, the needle guide 80 is removable from the mounting base 50. In certain such implementations, the needle guide 80 is disposable, while the mounting base 50 and bracket 80 are reused for multiple imaging procedures. While needle guide 80 may be disposable, it will be appreciated that even a "disposable" needle guide may be reused for more than one imaging analysis on the same patient, or may be sterilized between patients, if desired.

Alternatively, a new needle guide 80 is used for each medical procedure. It will be appreciated that the needle guide 80, consisting of a relatively small piece compared to the rest of the needle guide system 10, can have a reduced cost of operation over needle guide systems that have a large disposable piece. The cost savings may come in the form of reduced materials, but more significantly can come from having reduced cleaning and sterilization costs and cost savings coming from the reuse of essential components, particularly the mounting base 50, for multiple procedures.

Referring now to FIG. 2 and FIG. 3, a fragmentary elevational view and a fragmentary perspective view of a portion of the needle guide mounting base 50 are shown. In both figures, the mounting base 50 is depicted without the needle guide 80 so as to show the elements of the mounting base 50 that are configured to secure the needle guide 80. It should also be appreciated that FIG. 2 and FIG. 3 show opposing sides of the mounting base. FIG. 2 shows a first side 59 of the mounting base 50, and FIG. 3 shows a second side 60, of the mounting base 50.

As is evident from FIG. 2 and FIG. 3, the pivoting mounting base 50 has a pivoting portion 52 and a non-pivoting portion 54. Pivoting portion 52 is mounted generally within non-pivoting portion 54. Pivoting portion 52 is configured to pivot around an axis 53. Thus, pivoting portion 52 and non-pivoting portion 54 are secured to one another proximate axis 53.

It will also be appreciated that, in certain implementations of the present invention, a pin is positioned at axis 53 and runs through both the pivoting and non-pivoting portions of the mounting base 50. The pin may be made of any of numerous materials, including stainless steel, plastic, or other metal or polymer-based material. It will also be appreciated that pivoting portion 52 will, in some implementations, have a bore running through from first side 59 to second side 60. In other implementations, a channel, rather than a bore, runs along the pivoting portion 52 proximate the axis 53, and permits removal and insertion of the pivoting portion 52 from the non-pivoting portion 54 without removal of the pin in axis 53. In said embodiment, the pin remains secured to the non-pivoting portion 54 when the pivoting portion 52 is removed.

Pivoting portion 52 pivots in at least one axis to and away from the body 36 of the bracket. The direction of pivot is shown in FIG. 3, with arrows A–A'. In FIG. 2, the pivoting portion 52 is shown in an extend position wherein the pivoting portion is distal from the base 36. In contrast, in FIG. 3, the pivoting portion 52 is proximate the base 36. These orientations of the pivoting portion 52 are shown again in FIG. 4A and FIG. 4B, which are side elevational views of a disposable needle guide system constructed in accordance with the present invention. In FIG. 4A, like FIG. 2, the pivoting portion 52 is distal from the base 36; while in FIG. 4B, like FIG. 3, the pivoting portion 52 is proximate the base 36. The orientation shown in FIG. 2 and FIG. 4A permits the needle to enter tissue at a more acute angle with respect to the surface 16 of the patient 12 than the angle in FIG. 3 and FIG. 4B. It will also be appreciated that multiple angles may be chosen, and that the angles shown in the figures are demonstrative of such angles, but not exclusive. Other angles, both more acute and more oblique, are envisioned by the inventor as manners of practicing the present invention.

Referring now again to FIG. 2 and FIG. 3, the manner in which the pivoting portion 52 pivots within the non-pivoting portion 54 is evident. While pivoting portion 52 pivots with respect to non-pivoting portion 54, in certain implementations of the present invention a top surface 57 of the non-pivoting portion 52 comes in contact with the inner surface 71 of the non-pivoting portion 54 (See FIG. 2). The top surface 57 and inner surface 71 of the pivoting and non-pivoting portions 52, 54 frictionally engage one another in certain implementations of the present invention. The frictional engagement may be very minor, so as to simply provide a slight resistance during adjustment of the angle, or may be of a greater magnitude so as to hold the pivoting portion 52 in place during performance of the imaging analysis. It should also be appreciated that in certain implementations the top surface 54 of the pivoting portion 52 and the inner surface 71 of the non-pivoting portion 54 do not make contact with one another, and thus there is no friction between the two portions. A channel may be positioned within the inner surface 71 of the non-pivoting portion 54 to facilitate the alignment and stability of the non-pivoting portion 52 with respect to the pivoting portion 54. As such, the inner surface 71, in specific implementations, extends over the top surface 57 along the sides 59, 60 of the pivoting portion 52.

Referring again to FIG. 2 and FIG. 3, a locking pin 66 is shown as a mechanism for retaining the pivoting portion 52 in a selected position. Locking pin 66 extends through the outer surface 70 of the non-pivoting portion 54 and into the pivoting portion 52. Pin 66 is configured to travel along a channel 72 in the non-pivoting portion 54 of the mounting base 50. In certain embodiments, the pin 66 includes one or two side tabs 67, shown in FIG. 2 and FIG. 3. The side tabs 67 are configured to engage transverse slots 73 positioned in the outer surface 70 of the non-pivoting portion 54. The slots 73 are, in some embodiments, shallow depressions into which the tabs 67 may be placed in order to "lock" the pivoting portion 52 in place. While the embodiment depicted shows three different slots 73, more or less slots may be included in various embodiments of the present invention. Also, it will be appreciated that numbers, or other designations, may be made in the side of the mounting base 50 (as shown in FIG. 2) to designate the position of the pivoting portion 52. Such numbers or designations may be sequential integers, as shown, to depict a numerical slot position; or alternatively, the numbers may be an actual degree measurement indicating the incident angle of the needle or medical instrument as it enters the skin 16 of a patient 12 (not shown).

In operation, the embodiment depicted in FIG. 2 and FIG. 3 has the angle between the pivoting and non-pivoting portions 52, 54 adjusted by applying an upward force on the pin 66 (shown in FIG. 2), such that the side tabs 67 are lifted out of the transverse slots 73 (shown in FIG. 3), so that the pivoting portion may be moved (FIG. 3) to a new position, and the pin 67 pressed back into place to lock the pivoting portion 52 into a new position.

In certain implementations, a protective cover 40 (see FIG. 1) is positioned over the entire mounting base 50, including the pivoting and non-pivoting portions 52, 54. In such implementations, it is preferable that the pin 66 be easily adjusted through the cover 40. It will also be appreciated that in the embodiment depicted, the needle guide is further "locked" in place by the protective cover 40 when the protective cover 40 has elastic properties (such as with a latex material). In such embodiments, the elastic protective cover 40 applies a downward force as it stretches around the needle guide mounting base 50.

Continuing to refer to FIG. 2 and FIG. 3, the portion of the mounting base 50 that is configured to receive the needle guide 80 (shown in FIG. 1, 5A, and 5B) will be described. The mounting base 50 is configured such that a needle guide 80 may be secured to the base 50. In certain implementations of the present invention, the base 50 permits the mounting of the needle guide 80 with minimal kinetic friction, and uses a compressive force to retain the needle guide 80. Kinetic friction refers here to the friction generated when two surfaces move with respect to one another while in contact with one another. In the implementation shown in FIG. 2 and FIG. 3, the pivoting portion 52 is specifically configured to retain the needle guide 80. On each of the two sides 59, 60 is a receiver recess 61. In specific implementations, receiver recess 61 is a shallow depression, generally uniform in depth, along a portion of the first and second sides 59, 60. In addition, in the embodiment depicted, a locking recess 62 is shown in each of the receiver recesses 61. Locking recess 62 is a depression in the first and second sides 59, 60, even deeper than the receiver recesses 61. In specific implementations, the locking recesses 62 are generally concave depressions without abrupt transitions between the locking recesses 62 and the receiver recesses 61. In addition, it will be noted in FIG. 2 and FIG. 3 that the receiver recesses 61 have a transition ridge 63 along the periphery, at the junction of the receiver recess 61 and the surrounding first and second sides 59, 60 of the pivoting portion 52.

Figure 5A:
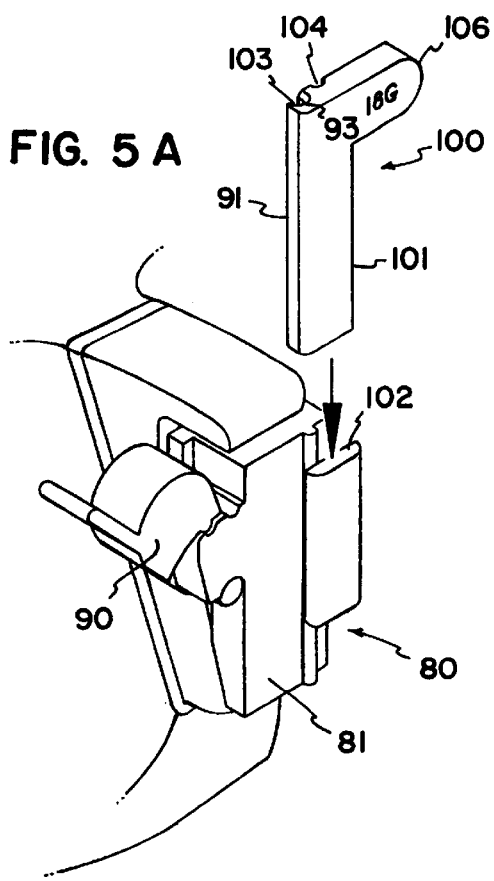
FIG. 5A is a perspective view of a disposable needle guide and mounting base constructed in accordance with the present invention, showing a retainer member removed from the needle guide.
Figure 5B:
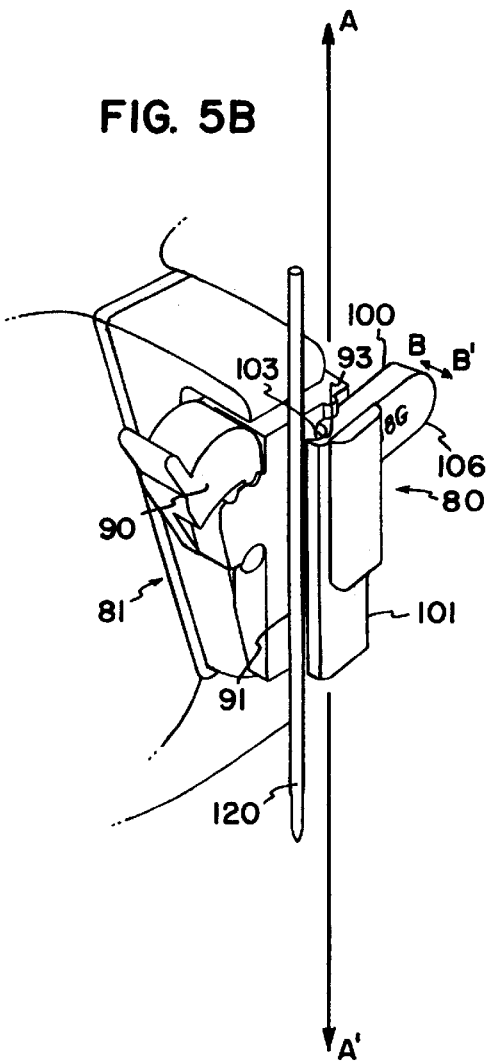
FIG. 5B is a perspective view of a disposable needle guide and mounting base constructed in accordance with the present invention, showing the retainer member inserted into the needle guide.

The receiver recesses 61 and the locking recesses 62, described above, are configured to retain the needle guide 80, shown in FIGS. 5A, 5B, 6, and 7. In FIG. 5A and 5B, the needle guide 80 is shown fitting over the mounting base 50. In certain implementations, a protective cover is positioned between the mounting base 50 and the needle guide 80.

Figure 6:
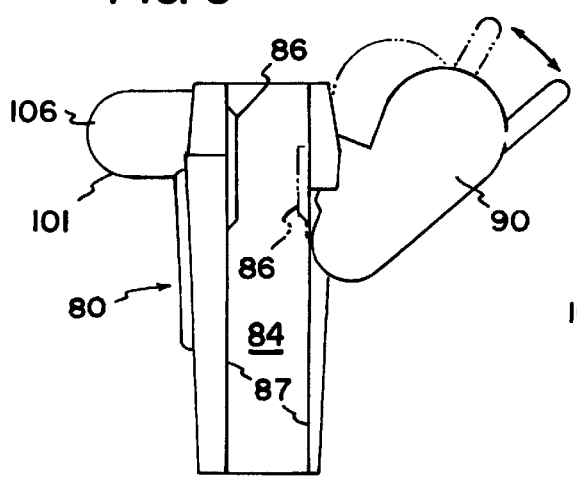
FIG. 6 is a back elevational view of a removable disposable needle guide constructed in accordance with the present invention.
Figure 7:
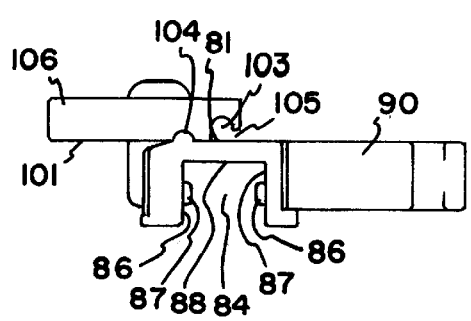
FIG. 7 is a top elevational view of a removable disposable needle guide constructed in accordance with the present invention.

The interior or back of the needle guide 80 is shown depicted in FIG. 6, with a top view shown in FIG. 7. In FIG. 6, the locking protrusions 86 are shown. These locking protrusions are configured to engage the locking recesses 62 of the pivoting portion 52. Likewise, the inner side walls 87 of the needle guide fit into the receiver recesses 61 of the pivoting portion 52, to give the configuration shown generally in FIG. 1. The inner back wall 88 of the needle guide 80 fits around the outer edge of the pivoting portion 52, such that the volume 84 defined by the inner side walls 87 and inner back wall 88 is occupied by part of the pivoting portion 52.

In the embodiment shown, the needle guide 80 is locked to the pivoting portion 52 of the mounting base 50 by moving the locking swivel 90 between a locked and unlocked position (see FIG. 6). In the locked position (shown in phantom lines in FIG. 6), the locking protrusion 86 integrally formed with the locking swivel 90 may enter and engage one of the locking recesses 62 of the pivoting portion 52. It will be observed that in FIG. 5A the locking swivel 90 is in an "unlocked" position permitting the removal of the needle guide 80; while in FIG. 5B the locking swivel 90 is in a "locked" position wherein the needle guide 80 is securely attached to the mounting base 50.

It will also be appreciated that in the present invention the retractable characteristic of the locking protrusion 86 of the locking swivel 90 allows for placement of a tight-fitting needle guide 80 over a protective cover 40 and mounting base 50 with low kinetic friction. Once in place over the mounting base, the locking swivel 90 is "locked" so as to press the two locking protrusions 86 into corresponding locking recesses 62, thereby securely retaining the needle guide 80 to the base 50. The friction between the pieces is reduced because the locking recess 86 on the locking swivel 90 is retracted during the attachment and removal process, thereby expanding the width of mounting socket 84 until the swivel 90 is locked in place. This design reduces the amount of "dragging" between the needle guide 80 and the cover 40 and mounting base 50, thereby preventing binding and potential puncture or damage to the cover 40.

Now, referring again to FIGS. 5A and 5B in particularity, the retainer member 100 that actually secures the needle 120 (or other similar medical instrument) is depicted. Retainer member 100 is shown removable from the body 81 of the needle guide 80. In FIG. 5A the retainer member 100 is shown lifted up and apart from the body 81 of the guide 80, while in FIG. 5B the retainer member 100 is shown inserted into retaining slot 102 (shown in FIG. 5A). The retainer member 100 includes both a foot 101 and a handle 106. Handle 106 is configured to be manually manipulated by a finger or hand.

A needle 120 is held by the needle guide 80 when the retainer member 100 is inserted into the retainer slot 102, as shown in FIG. 5B. The needle 120 is held between the retainer member 100 and the body 81. Specifically, in certain implementations, the needle is held in place in a needle receiving slot 103 in the retainer member 100 (see FIG. 5A and FIG. 5B). The needle receiving slot 103 runs along the length of the foot 101 of the retainer member 100.

The retainer member 100 pivots back and forth along axis A–A' by movement of the handle 106 as shown in FIG. 5B (See also FIG. 7). By pressing on handle 106, the retainer member 100 opens and closes along gap 105 (FIG. 7). Expanding gap 105 permits the insertion or removal of a needle when the handle 106 is depressed. Note that retainer member 100 is configured, in specific implementations, such that gap 105 is minimized when no force is applied to the handle. Thus, when a needle is inserted into the receiving slot 103, the foot 101 and the body 81 apply a compressive force against the needle 120. This compressive force helps retain the needle in place. In addition the fact that retainer member 100 pivots in the direction B–B' along axis A–A' allows for a plurality of different sized needles to be used with one retainer member 100. Alternatively, retainer members 100 having different sized needle receiving slots 103 may be used to place different sized needles into a patient.

It will also be appreciated that the present invention benefits from the fact that the needle 120 may be removed from side 91 of the needle guide by depressing the handle 106 without removal of the needle from the patient. Likewise, the needle 120 may be reinserted into the needle guide 80 through gap 105 without significant disruption or agitation of the needle. The needle 120 may also be removed from the needle guide 80 by lifting out from top 93 of the retainer member 100. This allows a second, third, or more needles (or other instruments) to be inserted into a patient with one needle guide. Notably, the present invention allows removal of the needle 120 from the needle guide 80 without rotation or other significant agitation or movement of the needle 120. The needles can even be installed at variable angles by adjusting the angle between the pivoting and non-pivoting portions 52, 54 in between placements of needles. It will also be noted that in the embodiments described, the protective cover is not impacted by the insertion or removal of the needles, thereby preserving the sterile conditions mentioned above.

While the embodiments described above secure the needle guide 80 to a pivoting portion 52 of a mounting base 50, it will also be appreciated that the needle guide 80 may be secured to a mounting base 50 that does not pivot, but rather has one secured position. While such embodiments may not include an adjustable angle, they still benefit from the attachment of a needle guide over a protective cover with reduced kinetic friction.

It will be appreciated that, although the implementation of the invention described above is directed to an ultrasound probe, the present device may be used with other non-invasive medical imaging systems, and is not limited to ultrasound probes. In addition, while the present invention has been described with reference to several particular implementations, those skilled in the art will recognize that many changes may be made hereto without departing from the spirit and scope of the present invention.

I claim:

1. A disposable needle guide system for guiding a needle into a patient undergoing imaging analysis, the disposable needle guide system comprising:
   a bracket for securing the needle guide system to an imaging instrument;
   a mounting base secured to the imaging instrument by the bracket;
   a pivoting portion of the mounting base configured to pivot along at least one axis; and
   a disposable needle guide configured to be removably secured to the pivoting portion of the mounting base, the needle guide having a needle retainer member configured to retain a needle by application of a clamping force between the needle retainer member and a first surface of the needle guide.

2. The disposable needle guide system of claim 1, wherein a protective cover may be placed over the bracket and mounting base, and the disposable needle guide is configured to be removably secured to the mounting base over the protective cover without the development of significant kinetic friction between the protective cover and the disposable needle guide.

3. The disposable needle guide system of claim 2, wherein the needle guide further comprises a movable locking member having an unlocked configuration in which the locking member does not apply pressure to the mounting base, and a locked configuration in which the locking member does apply pressure to the mounting base.

4. The disposable needle guide system of claim 1, wherein the pivoting portion of the mounting base pivots around an axis occupied by a pin.

5. The disposable needle guide system of claim 1, wherein the pivoting portion is integrally connected to a non-pivoting portion of the mounting base by a flexible connecting portion, and the pivoting portion pivots around an axis formed by flexing of the connecting portion.

6. The disposable needle guide system of claim 1, wherein the pivoting portion of the mounting base is configured to be locked in one of a plurality of pre-set positions.

7. The disposable needle guide system of claim 1, wherein the needle retainer member is slidably secured to the needle guide and is interchangeable with a second needle retainer member.

8. The disposable needle guide system of claim 1, wherein the needle retainer member is integrally formed with the needle guide.

9. The disposable needle guide system of claim 1, wherein a needle is removed from the needle guide by release of the clamping force.

10. The disposable needle guide system of claim 1, wherein the needle retainer member pivots along an axis parallel to the needle retainer member, permitting needles of multiple sizes to be held between the needle retainer member and the first surface of the needle guide.

11. The disposable needle guide system of claim 1, further comprising a plurality of interchangeable needle retainer members.

12. The disposable needle guide system of claim 1, wherein the bracket comprises paired arms for securing the needle guide system to an imaging instrument, the paired arms configured to apply a compressive force to the imaging instrument.

13. The disposable needle guide system of claim 1, wherein the imaging instrument is an ultrasound probe.

14. A locking member for locking a disposable needle guide to an imaging instrument with reduced strain on a sterile cover over the imaging instrument, the locking member comprising:
   a substantially rigid body configured to receive a needle guide;
   a mounting socket within the rigid body, the mounting socket including a depression in the substantially rigid body, the depression having first and second opposed sides;
   a locking swivel positioned to form a portion of the first side of the mounting socket, the locking swivel configured to move from an unlocked position in which the mounting socket has a first width and a locked position in which the mounting socket has a second width less than the first width.

15. The locking member for locking a disposable needle guide to an imaging instrument according to claim 14, wherein the locking member is secured to the imaging instrument over a protective cover without the development of significant kinetic friction between the protective cover and locking member.

16. The locking member for locking a disposable needle guide to an imaging instrument according to claim 14, wherein the locking swivel pivots along an axis.

17. The locking member for locking a disposable needle guide to an imaging instrument according to claim 14, wherein the locking member is formed of an injection molded thermoplastic.

18. A pivoting mounting base for securing a needle guide during imaging analysis, the pivoting mounting base comprising:

a non-pivoting portion configured to be retained on an imaging instrument;

a pivoting portion configured to receive a needle guide;

a locking pin for locking the pivoting portion at a specific position with respect to the non-pivoting portion; and wherein the pivoting portion may rotate with respect to the non-pivoting portion and the imaging instrument to align the needle guide at a desired angle to direct a needle toward a target identified by the imaging instrument.

19. The pivoting mounting base of claim 18, wherein the pivoting portion of the mounting base pivots around an axis occupied by a pin.

20. The pivoting mounting base of claim 18, wherein the pivoting portion is integrally connected to a non-pivoting portion of the mounting base by a flexible connecting portion, and the pivoting portion pivots around an axis formed by flexing of the connecting portion.

21. The pivoting mounting base of claim 18, wherein the pivoting portion of the mounting base is configured to be locked in one of a plurality of pre-set positions.

22. The pivoting mounting base of claim 18, wherein the pivoting portion and non-pivoting portion frictionally engage one another to provide resistance in movement of the pivoting portion with respect to the non-pivoting portion.

23. A needle guide for use in guiding a needle into a patient undergoing imaging analysis, the needle guide comprising:

a body formed of a substantially rigid material;

a needle retainer member configured to be removably secured to the body and further configured to apply a clamping force to between the needle retainer member and the body, the needle retainer having a needle retaining foot and a handle; and a needle receiving slot within the foot;

wherein a needle may be held between the body and needle retainer member by insertion into the needle retaining slot within the foot by application of a clamping force.

24. The needle guide for use in guiding a needle according to claim 23, wherein the needle retainer is removable.

25. The needle guide for use in guiding a needle according to claim 23, wherein the needle retainer can fit various sized needles.

26. The needle guide for use in guiding a needle according to claim 23, wherein the needle retainer is interchangeable.

* * * * *